United States Patent
Kalantar-Zadeh et al.

(10) Patent No.: US 9,638,705 B2
(45) Date of Patent: May 2, 2017

(54) PROGNOSTIC ASSAYS FOR MAINTENANCE HEMODIALYSIS PATIENTS

(75) Inventors: Kamyar Kalantar-Zadeh, Torrance, CA (US); Michael P. Caulfield, San Clemente, CA (US); Wael A. Salameh, San Juan Capistrano, CA (US)

(73) Assignees: QUEST DIAGNOSTICS INVESTMENTS INCORPORATED, Wilmington, DE (US); LOS ANGELES BIOMEDICAL RESEARCH INSTITUTE, Torrance, CA (US)

( * ) Notice: Subject to any disclaimer, the term of this patent is extended or adjusted under 35 U.S.C. 154(b) by 353 days.

(21) Appl. No.: 13/283,536

(22) Filed: Oct. 27, 2011

(65) Prior Publication Data
US 2012/0103072 A1    May 3, 2012

Related U.S. Application Data

(60) Provisional application No. 61/409,003, filed on Nov. 1, 2010.

(51) Int. Cl.
*G01N 33/00* (2006.01)
*G01N 33/92* (2006.01)

(52) U.S. Cl.
CPC ......... *G01N 33/92* (2013.01); *G01N 2800/50* (2013.01)

(58) Field of Classification Search
CPC .................. G01N 2800/50; G01N 33/92
USPC .................. 204/549, 645; 73/61.52; 702/19; 436/71
See application file for complete search history.

(56) References Cited

U.S. PATENT DOCUMENTS

| | | | |
|---|---|---|---|
| 5,925,229 A | 7/1999 | Krauss et al. | |
| 6,727,102 B1 * | 4/2004 | Holvoet et al. | 436/501 |
| 7,259,018 B2 | 8/2007 | Benner et al. | |
| 7,514,213 B2 | 4/2009 | Qu et al. | |
| 7,713,744 B2 | 5/2010 | Benner et al. | |
| 2003/0136680 A1 * | 7/2003 | Benner et al. | 204/549 |
| 2008/0121025 A1 * | 5/2008 | Okazaki | 73/61.52 |
| 2008/0302666 A1 | 12/2008 | Benner et al. | |
| 2008/0305549 A1 | 12/2008 | Caulfield et al. | |

OTHER PUBLICATIONS

Rajman et al. LDL particle size: an important drug target.(1999). Clinical Pharmacology.48:125-133.*
Caulfield et al., "Letters to the Editor," Clinical Chemistry, (2008), 15:12.
Cromwell et al., "Low-density lipoprotein particle number and risk for cardiovascular disease," Curr. Atheroscler. Rep. 2004, 6(5):381-387.

(Continued)

*Primary Examiner* — Rebecca M Fritchman
(74) *Attorney, Agent, or Firm* — Foley & Lardner LLP

(57) ABSTRACT

Described herein are methods for determining the overall survival of maintenance hemodialysis patients. The methods include measuring low density lipoprotein (LDL) particle size and subfraction concentrations as prognostic tools for early mortality risk detection. For example, the presence of increased very small LDL concentration or decreased LDL particle size in blood-serum serves as a useful means for prognostic risk assessment and monitoring.

18 Claims, 4 Drawing Sheets

(56) References Cited

OTHER PUBLICATIONS

Giles et al., "A prognostic model for survival in chronic lymphocytic leukaemia based on p53 expression," British Journal of Haematology, 2003, 121:578-585.

Grambsch et al., "Diagnostic Plots to Reveal Functional Form for Covariates in Multiplicative Intensity Models," Biometrics, Dec. 1995, 51(5):1469-1482.

Iseki et al., "Hypocholesterolemia is a significant predictor of death in a cohort of chronic hemodialysis patients," Kidney Int., 2002, 61:1187-1193.

Kalantar-Zadeh et al., "A matched comparison of serum lipids between hemodialysis patients and nondialysis morbid controls," Hemodialysis Int'l., (2005), 9:314-324.

Kalantar-Zadeh et al., "HDL-inflammatory index correlates with poor outcome in hemodialysis patients," Kidney Int., 2007, 72:1149-1156.

Kilpatrick et al., "Association between Serum Lipids and Survival in Hemodialysis Patients and Impact of Race," J. Am. Soc. Nephrol., 2007, 18:293-303.

Kovesdy et al., "Inverse Association between Lipid Levels and Mortality in Men with Chronic Kidney Disease Who Are Not Yet on Dialysis: Effects of Case Mix and the Malnutrition-Inflammation-Cachexia Syndrome," J. Am. Soc. Nephrol., 2007, 18:304-311.

Liu et al., "Association Between Cholesterol Level and Mortality in Dialysis Patients: Role of Inflammation and Malnutrition," JAMA, 2004, 291(4):451-459.

Maheshwari et al., "Pattern of Lipid Profile in Patients on Maintenance Hemodialysis," Saudi J. Kidney Dis. Transpl., 2010, 21(3):565-570.

Mekki et al., "Long term hemodialysis aggravates lipolytic activity reduction and very low density, low density lipoproteins composition in chronic renal failure patients," BMC Card. Dis., 2009, 9:41.

Miller et al., "Association of Hemodialysis Treatment Time and Dose With Mortality and the Role of Race and Sex," Am. J. Kidney Dis., 2010, 55(1): 100-112.

Otvos et al., "Concerns Regarding Lipoprotein Particle Measurement by Ion Mobility Analysis," Clinical Chemistry, 2008, 54(12):2086-2087.

Rambod et al., "Association of serum prealbumin and its changes over time with clinical outcomes and survival in patients receiving hemodialysis," Am. J. Clin. Nutr., 2008, 88:1485-1494.

\* cited by examiner

PROGNOSTIC ASSAYS FOR MAINTENANCE HEMODIALYSIS PATIENTS

CROSS-REFERENCE TO RELATED APPLICATIONS

This application claims benefit of U.S. Provisional Application No. 61/409,003, filed Nov. 1, 2010, which is hereby incorporated by reference in its entirety.

STATEMENT OF GOVERNMENT SPONSORED RESEARCH

This invention was made with United States government support awarded by the following agencies: National Institutes of Health, National Institute of Diabetes, Digestive and Kidney Disease grants # R21-DK61162 and K23-DK061162, and National Centers for Research Resources, National Institutes of Health General Clinical Research Center (GCRC) grant # M01-RR00425. The United States government has certain rights in the invention.

TECHNICAL FIELD

The present invention generally relates to methods for predicating and determining overall survival for maintenance hemodialysis (MHD) patients. The methods described herein include measuring the properties of lipoproteins in MHD patients.

BACKGROUND OF THE INVENTION

The following description is provided to assist the understanding of the reader. None of the information provided or references cited is admitted to be prior art.

End stage renal disease (ESRD) is the manifestation of a chronic kidney disease characterized by complete kidney failure or an imminent progression thereto. There are a number of treatments for ESRD including hemodialysis, peritoneal dialysis, and kidney transplantation. Hemodialysis, however, is the primary therapy for patients with ESRD. Approximately seventy percent of ESRD patients require chronic, maintenance hemodialysis (MHD). The aim of MHD treatment is to replace kidney function with long-term hemodialysis intervention. MHD decreases nephrological degradation by removing contaminants from the blood and maintaining appropriate blood volume. Hemodialysis is performed by using a dialysis machine that pumps blood from a patient, through a dialyzer, and then back into the patient. Accordingly, hemodialysis therapy is an extracorporeal process that cleanses a patient's blood.

The number of maintenance dialysis patients in the United States is currently over 400,000 and still growing fast. Two thirds of all dialysis patients die within 5 years of initiation of dialysis treatment, a 5-year survival worse than that of many cancers. Approximately half of all dialysis patients die of cardiovascular disease (CVD). In the general population conventional serum levels of LDL cholesterol (LDL-C) and HDL cholesterol (HDL-C) predict incident atherosclerotic CVD. Nevertheless, similar to individuals with chronic heart failure (CHF), the conventional CVD risk factors such as hypercholesterolemia are not associated with mortality in these patients; indeed in both dialysis and CHF patients, a low, rather than a high, serum total cholesterol (TC) or LDL-C is associated with higher mortality, a phenomenon known as lipid paradox or reverse epidemiology. Hence, alternative CVD biomarkers including alternative lipid measures are needed to more reliably risk-stratify dialysis or CHF patients.

Each lipoprotein class consists of a continuous spectrum of particles of different size, density, metabolism, and atherogenic impact. Various studies have evaluated the associations of small LDL subfraction concentration, total LDL particle concentration (LDL-Pc), specific HDL subfractions, and combined measures such as the LDL-C/HDL-C and apoB/apoA-I ratios with cardiovascular risk. However studies on chronic kidney disease (CKD) patients are scarce and often limited to conventionally measured TC and LDL-C.

SUMMARY OF THE INVENTION

The present invention provides a method for predicting the overall survival of a maintenance hemodialysis patient comprising: measuring one or both of LDL particle size and LDL subfraction concentration(s) (e.g., vs-LDL and/or l-LDL) in a sample from the patient, wherein a difference in one or both of LDL particle size and LDL subfraction concentration compared to a reference level is an indication of the overall survival of the patient.

In one aspect, the invention provides a method for predicting mortality risk in a maintenance hemodialysis patient by:
 a. measuring the very small low density lipoprotein (vs-LDL) concentration in a sample from the patient,
 b. comparing the sample vs-LDL concentration measured in step (a) with a reference vs-LDL concentration, and
 c. identifying the patient as having increased risk of mortality when the sample vs-LDL concentration is greater than the reference vs-LDL concentration or identifying the patient as having no change in the risk of mortality when the sample vs-LDL concentration is less than or equal to the reference vs-LDL concentration.

In another aspect, the invention provides a method for predicting mortality risk in a maintenance hemodialysis patient by:
 a. measuring the large low density lipoprotein (l-LDL) concentration in a sample from the patient,
 b. comparing the sample l-LDL concentration measured in step with a reference l-LDL concentration, and
 c. identifying the patient as having reduced risk of mortality when the sample l-LDL concentration is greater than the reference l-LDL concentration or identifying the patient as having no change in the risk of mortality when the sample l-LDL concentration is less than the reference l-LDL concentration.

In another aspect, the invention provides a method for predicting mortality risk in a maintenance hemodialysis patient by:
 a. measuring the very small low density lipoprotein (vs-LDL) concentration and the large low density lipoprotein (l-LDL) concentration in a sample from the patient,
 b. comparing the sample vs-LDL concentration measured in step (a) with a reference vs-LDL concentration and comparing the sample l-LDL concentration measured in step (a) with a reference l-LDL concentration,
 c. identifying the patient as having
   i. increased risk of mortality when the sample vs-LDL concentration is greater than the reference vs-LDL concentration,
   ii. reduced risk of mortality when the sample l-LDL concentration is greater than the reference l-LDL concentration, or iii. no change in the risk of mortality when the sample vs-LDL concentration is less than the reference vs-LDL concentration and the l-LDL concentration is less than or equal to the reference l-LDL concentration.

In one embodiment of any of the foregoing aspects, the reference vs-LDL concentration is about 121 nmol/L and or the reference l-LDL concentration is about 105 nmol/L. In other embodiments, either one or both of the reference vs-LDL concentration and reference l-LDL concentration are derived from a control population of subjects not undergoing maintenance hemodialysis. Alternatively, one or both of the reference vs-LDL concentration and reference l-LDL concentration are the concentrations measured in the same patient at an earlier time or in the same patient prior to receiving treatment.

In another aspect, the invention provides a method for predicting mortality risk in a maintenance hemodialysis patient comprising:
a. measuring the low density lipoprotein (LDL) particle size in a sample from the patient,
b. comparing the sample LDL particle size measured in step (a) with a reference LDL particle size, and
c. identifying the patient as having increased risk of mortality when the sample LDL particle size is less than the reference LDL particle size or identifying the patient as having no change in the risk of mortality when the sample LDL particle size is greater than or equal to the reference LDL particle size.

In one embodiment, the measured LDL particle size is the mean LDL particle size. Preferably, the reference mean LDL particle size within the range of about 216 Å to about 224 Å. In some embodiments, the reference mean LDL particle size is at least about 216 Å, 218 Å, 219 Å, 220 Å, 222 Å, 224 Å, or more. The reference LDL particle size may be derived from a control population of subjects not undergoing maintenance hemodialysis. Alternatively, the reference LDL particle size is the LDL particle size measured in the same patient at an earlier time or in the same patient prior to receiving treatment.

In another aspect, the invention provides a method for predicting mortality risk in a maintenance hemodialysis patient by:
a. measuring the high density lipoprotein (HDL) concentration in a sample from the patient,
b. comparing the sample HDL concentration measured in step (a) with a reference vs-HDL concentration, and
c. identifying the patient as having increased risk of mortality when the sample HDL concentration is greater than the reference HDL concentration or identifying the patient as having no change in the risk of mortality when the sample HDL concentration is less than or equal to the reference HDL concentration.

In some embodiments, the reference HDL concentration is in the range of about 2,000-3,500 nmol/L, about 2,500-3,300 nmol/L, about 2,800-3,100 nmol/L, or about 2850-3000 nmol/L. In some embodiments, the reference HDL concentration is about 2,500, 2,600, 2,700, 2,800, 2,900, 2,919, 3,000, 3,100, 3,200, 3,300 nmol/L or more. In other embodiments, the reference HDL concentration is derived from a control population of subjects not undergoing maintenance hemodialysis. Alternatively, the reference HDL concentration is the concentration measured in the same patient at an earlier time or in the same patient prior to receiving treatment.

In another aspect, the invention provides a method for predicting mortality risk in a maintenance hemodialysis patient by:
a. measuring the large low density lipoprotein (l-LDL) particle concentration and the small low density lipoprotein (s-LDL) particle concentration in a sample from the patient,
b. determining the ratio of the l-LDL concentration to the s-LDL concentration, and
c. identifying the patient as having reduced risk of mortality when the sample l-LDL:s-LDL ratio is greater than the reference ratio or identifying the patient as having no change in the risk of mortality when the reference l-LDL:s-LDL ratio is less than the reference ratio.

In some embodiments, the reference l-LDL:s-LDL ratio is in the range of about 0.75-125, or about 0.80-1.15, or about 0.85-1.10, or about 0.90-1.05, or about 0.95-1.00. In some embodiments, the reference l-LDL:s-LDL ratio is about 0.75, 0.80, 0.85, 0.90, 0.95, 0.97, 1.00, 1.05, 1.10, 1.15, 1.20, 1.25, or more. In other embodiments, the reference l-LDL:s-LDL ratio is derived from a control population of subjects not undergoing maintenance hemodialysis. Alternatively, the reference l-LDL:s-LDL ratio is the ratio measured in the same patient at an earlier time or in the same patient prior to receiving treatment.

In other embodiments of any of the foregoing aspects, the sample is whole blood, serum, or plasma. The sample LDL and HDL concentrations, including the subfraction concentrations (e.g., vs-LDL concentration and l-LDL concentration) and/or the LDL particle size may be measured by ion mobility analysis.

Optionally, the methods of the invention may further comprising the step of selecting a treatment regime based upon mortality risk of the patient.

BRIEF DESCRIPTION OF THE FIGURES

(FIG. 2A) unadjusted; (FIG. 2B), adjusted for case-mix+lipids+MICS+inflammation. Case-mix included age, gender, race/ethnicity, diabetes mellitus, dialysis vintage, modified Charlson comorbidity score and dialysis dose (single pool Kt/V). Lipids included LDL and HDL cholesterol concentration and TG. Malnutrition-inflammation complex syndrome (MICS) variables included serum or blood levels of phosphorus, albumin, creatinine, calcium, ferritin, hemoglobin, normalized protein catabolic rate (nPCR), also known as normalized protein nitrogen appearance (nPNA); and body mass index. Inflammatory markers include serum concentrations of C-reactive protein (CRP), IL-6, and TNF-α.

DETAILED DESCRIPTION

Figure 1:
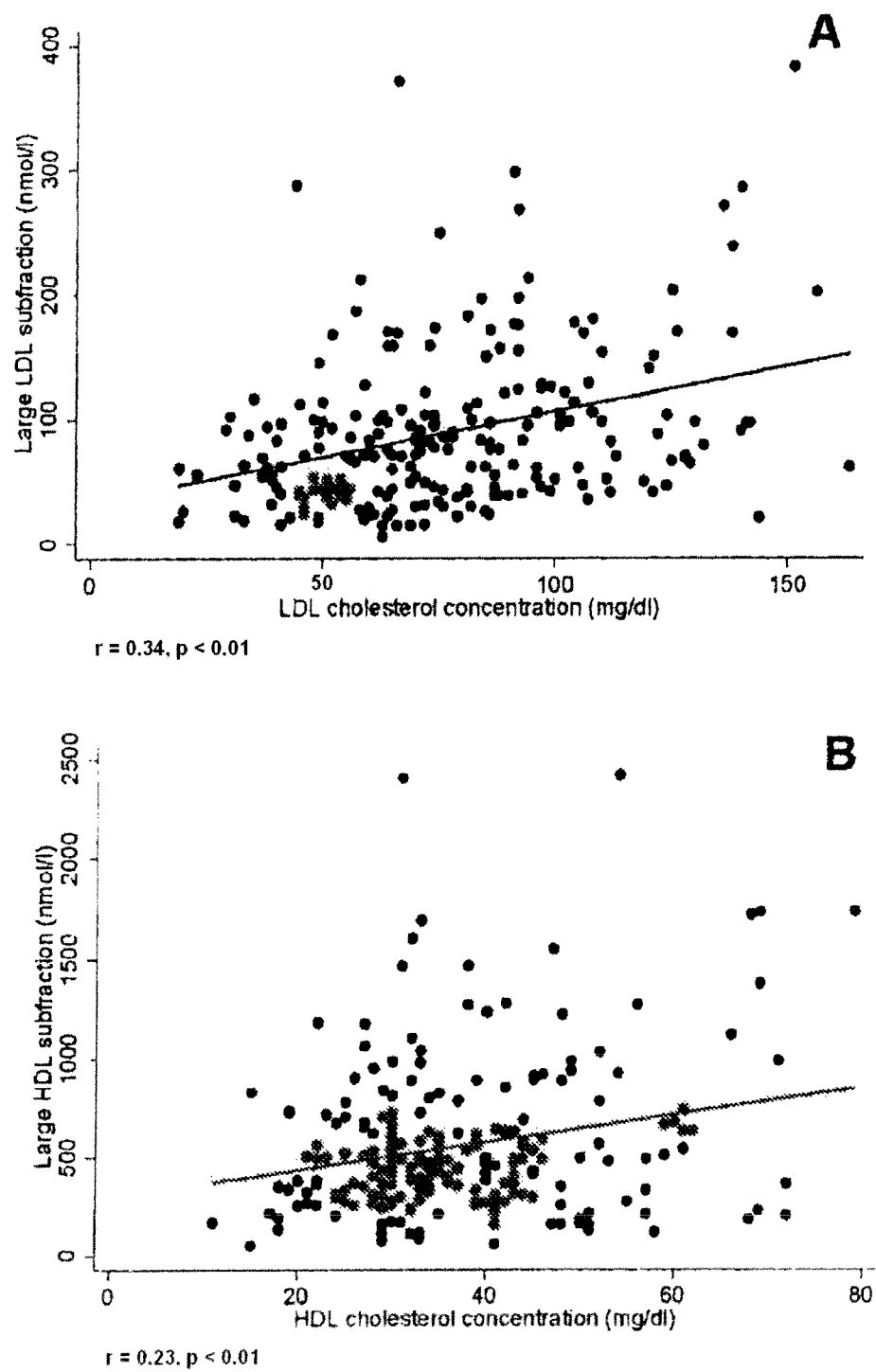
FIG. 1 is a series of scatter plots (including the regression line and 95% confidence intervals) showing the correlations of serum LDL (FIG. 1A) and HDL (FIG. 1B) cholesterol concentrations with large LDL and HDL subfraction concentrations.

The present inventions are based on the identification that, in maintenance hemodialysis (MHD) patients, smaller sized LDL-Pd and higher concentrations of very small LDL-P are associated with increased mortality, whereas higher concentration of larger sized LDL-P is associated with decreased risk of death. Accordingly, in some aspects, the invention provides methods for determining overall survival in MHD patients based at least partially on lipoprotein analysis of MHD patient samples. Further disclosed herein are methods for predicting mortality based on the measurement of lipoprotein properties from a sample. Specifically, the present invention generally describes for the measurement of LDL particle size and subfraction concentration MHD patients.

As used in this specification and the appended claims, the singular forms "a", "an", and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. For example, when referring to the mean LDL particle size, "about" refers to ±1-5 Å. When referring to LDL concentrations, "about" will mean up to ±5-10% of the enumerated value.

As used herein, the term "biomarker" or "LDL property" or "properties of LDL" in the context of the present invention refers to a LDL concentration, particle size, or combination thereof, or a LDL subfraction concentration, particle size, or combination thereof, including, but not limited to, lame LDL and very small LDL, which is differentially present in a sample taken from MHD patients as compared to a comparable sample taken from a control subject or a population of control subjects, or as compared to a reference level or value.

The term "clinical factors" as used herein, refers to any data that a medical practitioner may consider in determining a diagnosis or prognosis of disease. Such factors include, but are not limited to, the patient's medical history, a physical examination of the patient, complete blood count, etc.

The term "comparable" or "corresponding" in the context of comparing two or more samples, means that the same type of sample, e.g., whole blood, is used in the comparison. For example, a LDL level in a sample of whole blood can be compared to a LDL level in another whole blood sample. In some embodiments, comparable samples may be obtained from the same individual at different times. In other embodiments, comparable samples may be obtained from different individuals, e.g., a patient and a healthy individual. In general, comparable samples are normalized by a common factor. For example, body fluid samples are typically normalized by volume body fluid and cell-containing samples are normalized by protein content or cell count.

As used herein, the term "control population" refers to individuals not undergoing maintenance hemodialysis or with a negative diagnosis or undetectable kidney disease, i.e., normal or healthy subjects.

The terms "determining," "measuring," "assessing," "assaying" are used interchangeably and include both quantitative and qualitative determinations. These terms refer to any form of measurement, and include determining if a characteristic, trait, or feature is present or not. Assessing may be relative or absolute, "Assessing the presence of" includes determining the amount of something present, as well as determining whether it is present or absent.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e., there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical arts for a particular disease or disorder, e.g., end stage kidney disease, wherein a patient is undergoing MHD.

As used herein, the phrase "difference of the level" or "difference in properties" refers to differences in the properties or a quantity of an LDL biomarker present in a sample taken from MHD patients as compared to a control. In one embodiment, a biomarker can be a LDL property or level which is present at an elevated amount or at a decreased amount in samples of MHD patients compared to a reference level.

As used herein, the term "ion mobility analysis" or "IMA" refers to the measurement of non-covalently bound particles that are processed through a system while maintaining their properties. For example, a sample is placed in a pressurized chamber of an IMA apparatus. Subsequently, the sample is exposed to dry gas and alpha radiation, thereby forming singly charged droplets. In one embodiment, the droplets are the particles that are measured. Once a relationship is determined between particle size and density, size or mobility distributions can then be converted into distributions of particle mass, density ($\mu g/cm^3$), and/or concentration, and the like. Accordingly, IMA allows for particle size and concentration to be determined in a sample of lipoprotein particles, e.g., VLDL, IDL, LDL, HDL and their subclasses and/or subfractions.

As used herein, the term "lipoprotein" or "lipoprotein particle" refer to particles obtained from mammalian blood which include apolipoproteins biologically assembled with noncovalent bonds to package for example, without limitation, cholesterol and other lipids. Lipoproteins typically refer to biological particles having various sizes, and include very low density lipoproteins (VLDL), intermediate density lipoproteins (IDL), low density lipoproteins (LDL), lipoprotein (a), high density lipoproteins (HDL) and chylomicrons.

As used herein, "VLDL", "IDL" "LDL", and "HDL" refer to classifications of lipoproteins. It is understood that the values for particle diameter may be determined by gel electrophoresis methods, as known in the art, or mobility analysis methods. With ion mobility analysis methods it has been observed that lipoprotein diameters can be smaller relative to diameters obtained with gel electrophoresis.

As used herein, the term "population" may be any group of at least two individuals. A population may include, e.g., but is not limited to, a control population, a patient population, a reference population, a population group, a family population, a clinical population, and a same sex population.

As used herein, the term "overall survival" or "OS" is used to refer to time in years from surgery to death from any cause. The calculation of this measure may vary depending on the definition of events to be either censored or not considered.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition.

As used herein, the term "reference level" refers to a level of a substance which may be of interest for comparative purposes. In one embodiment, a reference level may be the size or concentration of a lipoprotein expressed as an average of the size or concentration of a lipoprotein from samples taken from a control population of healthy (disease-free) subjects. In one embodiment, the reference level may be the level in the same subject at a different time, e.g., before the present assay, such as the level determined prior to the subject developing the disease or prior to initiating therapy. In general, samples are normalized by a common factor. For example, body fluid samples are normalized by volume body fluid and protein or cell-containing samples are normalized by protein content or the like.

As used herein, the term "sample" or "test sample" refers to any liquid or solid material containing lipoproteins. In one embodiment, a sample is obtained from a biological source, i.e., a "biological sample", such as blood or a fluid sample from an animal, most preferably, a human.

As used herein, the term "subject" refers to a mammal, such as a human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. The term "patient" refers to a "subject" who is, or is suspected to be, on MHD or afflicted with ESRD.

The phrase "substantially the same as" in reference to a comparison of one value to another value for the purposes of clinical management of a disease or disorder means that the values are statistically not different. Differences between the values can vary, for example, one value may be within 20%, within 10%, within 5%, within 2.5%, or within 1% of the other value.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

Sample Collection, Preparation, and Purification

The methods described herein provide for the measurement of LDL properties from a sample obtained from a MHD patient. Samples may be obtained using standard procedures and can be employed immediately or stored, under conditions appropriate for the type of sample, for later use. Following collection and preparation, the sample is subjected to analysis of lipoproteins, wherein the resulting LDL measurements allow for the prognostic determination of a MHD patient's overall survival.

The starting material for the methods described herein is typically a clinical sample, which is obtained from a MI-ID patient. Subsequently, LDL is separated from proteins and other biological constituents in the original sample. Purification methods known in the art may be used in the context of the present invention.

Methods for obtaining samples are well known to those of skill in the art and include, but are not limited to, aspirations, tissue sections, swabs, drawing of blood or other fluids, surgical or needle biopsies, and the like. The sample may be obtained from a subject, individual, or patient. The sample may contain cells, tissues or fluid obtained from a MHD patient. The sample may be a cell-containing liquid or a tissue. Samples may include, but are not limited to, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

In one embodiment, the lipoproteins derive from a plasma or serum sample, that has been purified. In one embodiment, plasma is the fluid obtained upon separating whole blood into solid and liquid components. In one embodiment, serum is the fluid obtained upon separating whole blood into solid and liquid components after it has been allowed to clot. In one embodiment, the plasma and/or serum is obtained from a MHD patient. In one embodiment, the plasma and/or serum, is obtained by withdrawing or otherwise collecting a biological tissue or fluid including, e.g., whole blood, serum and plasma.

In one embodiment, the sample is purified prior to analysis. To this end, the methods provide for isolation and/or purification of lipoproteins, initial sample collection, and preparation. In one embodiment, a 2 to 5 ml fasting blood specimen is initially obtained. Chylomicrons are not typically present in subjects who have been fasting for a period of at least 12 hours; thus, chylomicrons are eliminated by fasting. In one embodiment, the specimen is then subjected to centrifugation, via a clinical centrifuge, for approximately 10 minutes (min) at approximately 2000× G. In one embodiment, the centrifugation is sufficient to remove the cellular debris, i.e., unwanted cellular components, from the specimen. During this process, the more dense cellular components stratify at the bottom of the sample. A remaining less dense plasma specimen containing lipoproteins on top is then drawn off using methods well known in the art, aspiration.

In one embodiment, in preparation for centrifugation, a sample, e.g., plasma specimen, is adjusted to a specific density using high purity solutions or solids of inorganic salts, e.g., sodium chloride (NaCl), sodium bromide (NaBr), and the like. In one embodiment, the specific density is chosen to be greater than or equal to the highest density of the lipoprotein material to be analyzed, i.e., so that the lipoprotein material floats subsequent to density stratification. In one embodiment, the adjusted sample is ultracentrifuged, e.g., for approximately 18 hours (h) at 100,000× G, thereby separating the non-lipoprotein proteins from the lipoproteins. Non-lipoprotein proteins are removed from a sample, e.g., the plasma specimen via ultracentrifugation. Accordingly, the lipoproteins float to the top of the sample during ultracentrifugation. Thus, by sequentially centrifuging from the lowest density to highest density of the adjusted sample, the various classes and subclasses of lipoproteins can be sequentially extracted. In one embodiment, a dialysis step follows the extraction of a centrifuged sample to remove any salts that were previously introduced to the sample. In one embodiment, the dialysis step is performed for 4-12 h under conditions well known in the art.

In one embodiment, conditions for centrifugation for lipoprotein-containing samples described herein are well known in the art of biochemical separation. For example, samples are typically centrifuged at 10° C. for 1-4 h at 223,000× G. In one embodiment, centrifugation employs centrifugal force of between about 50,000-100,000, 100,000-120,000, 120,000-150,000, 150,000-200,000, 200,000-230,000, 230,000-250,000× G, or even higher force. In one embodiment, the time of centrifugation is about 1, 2, 2.2, 2.4, 2.6, 2.8, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18 h, or even longer. In one embodiment, prior to analysis by ion mobility, an aliquot of the lipid fraction is removed, e.g., 10-200 µL, from the top of the centrifuge tube and diluted, e.g., 1:800, in 25 mM ammonium acetate, 0.5 mM ammonium hydroxide, at a pH 7.4.

In one embodiment, the density of the solution is a value less than or equal to about 1.21 g/mL while centrifuging, this improves recovery, hence purification, of LDL. In one embodiment, the lipoproteins that are subjected to further purification are selected from the group consisting of HDL, LDL, IDL, Lp(a), and VLDL. In one embodiment, the lipoproteins are LDL, including subfractions thereof.

In one aspect, the present invention provides methods for analyzing the concentration and/or size distribution of lipoproteins, lipoprotein particles, and lipoprotein subfractions, e.g., LDL, LDL particle size, very small LDL concentration, and large LDL concentration, by ion mobility analysis. In one embodiment, LDL particle size includes, but is not limited to, sizes between about 0-1000, 0-500, 100-400, 150-350, 200-250, and 215-230 angstroms (Å). In one embodiment, very small LDL is a subfraction of total LDL.

In one embodiment, very small LDL is LDL that is less than about 230, 225, 220, 215, 210, or 205 Å. In one embodiment, very small LDL is LDL that is less than about 219 Å. In one embodiment, large LDL is a subfraction of total LDL. In one embodiment, large LDL is greater than about 220, 225, 230, 235, 240, or 245 Å. In one embodiment, large LDL is LDL that is greater than about 230 Å.

In one aspect, ion mobility analysis provides for analyzing particles in aerosols, biological solutions, or the like. Ion mobility analysis has been adapted to analyze various large and small biological macromolecules. Moreover, ion mobility analysis can be adapted to measure various biological particles as described herein, and as previously described. See e.g., U.S. Pat. Nos. 7,514,213; 7,259,018; 7,713,744; and U.S. Pat. App. Pub. Nos.: 2008/0305549; 2008/0302666; and 2003/0136680, all of which are herein incorporated by reference in their entirety. Ion mobility analysis is also known as ion electrical mobility or charged-particle mobility.

In one embodiment, analysis of biological particles includes employing an ion mobility analysis apparatus. Following ultracentrifugation, a sample is placed into a pressurized chamber. In one embodiment, a high voltage variable power supply positively biases the sample in the pressurized chamber. The positive bias and higher relative pressure allows for particle droplets to emit from the pressurized chamber. Once the droplets are formed, a dry gas is employed to propel the droplets into an emission region of an alpha radiation source, thereby reducing the charge state of the droplets to no more than one positive charge per droplet. In one embodiment, the charged droplets may be obtained using other methods to achieve a uniform charge state of no more than a single positive charge. In one embodiment, an alternating current corona, which produces secondary electrons having the same charge state reduction as an alpha source, is employed.

After charge reduction, the dry gas propels the particles into a differential mobility analyzer. A laminar flow excess gas, and an additional dry gas flow, is introduced into the analyzer to match the velocity of the dry gas flow. In one embodiment, varying the high voltage power supply allows for the particles, carried by the combined flows, to be incorporated into a mobility selected particle flow, which in turn flows into a particle counter. In one embodiment, the particle counter analyzes particle mobility and corresponding particle size. The particle counter is typically linked with a computer system for further analysis and data storage.

In one embodiment, ion mobility analysis allows for non-covalently bound biological particles to be processed through a system without losing their biological properties or degrading. In one embodiment, lipoprotein particles, e.g., VLDL, IDL, LDL, HDL and their subclasses and/or subfractions, are rapidly processed, thereby avoiding lipoprotein particle degradation. Once a relationship is known between particle size and density, size or mobility distributions are then converted into distributions of: particle mass; density µg/cm$^3$ of original plasma; number of particles in a size interval; and/or amount of particle mass in a size interval. Accordingly, ion mobility analysis allows for LDL particle size and subfraction concentrations to be determined in a sample.

In one aspect, analysis of biological particles is by gel electrophoresis. Gel electrophoresis is a technique used to separate charged molecules or particles according to their physical properties, i.e., charge or mass. As the particles are forced through a sieving gel matrix by an electrical current, they are separated based on their size and charge. Following ultracentrifugation, a sample containing lipoproteins is separated according to particle size using gel electrophoresis. In one embodiment, nondenaturing gradient gel electrophoresis is employed, Gradient gels employ an increasing percentage of matrix, e.g., polyacrylamide, in one direction to allow for increased separation of particles with similar properties. In one embodiment, variable rate density gradient gel electrophoresis is employed. See e.g., U.S. Pat. No. 5,925,229. In one embodiment, calibration markers are concomitantly separated on the gel, thereby allowing for the determination of LDL particle size. In one embodiment, due to the small variations in the sphericity among lipoprotein species, the migration distance of each particle is inversely related to particle size. It is well known in the art that polyacrylamide or agarose gel electrophoresis may be employed, at various percentages, for suitable separation of molecules or particles. Lipoprotein concentration, defined by particle size relative to the calibration marker, is determined by integration of the area of its peak on a densitometry scan. Accordingly, a corresponding particle size and subfraction concentration can be calculated for a lipoprotein, LDL or a subfraction thereof.

Determining Prognosis

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of LDL particle size and/or LDL subfraction concentration levels can be made, and a temporal change in activity can be used to determine a prognosis. For example, comparative measurements are made of the LDL particle size or LDL subfraction concentration of a body fluid in a patient at multiple time points, and a comparison of a value at two or more time points may be indicative of a particular prognosis.

A prognosis is often determined by examining one or more clinical factors and/or symptoms that correlate to patient outcomes. As described herein, the LDL particle size and/or LDL subfraction concentration is a clinical factor useful in determining prognosis. The skilled artisan will understand that associating a clinical factor with a predisposition to an adverse outcome may involve statistical analysis.

In certain embodiments, the levels of LDL particle size and/or LDL subfraction concentration are used as indicators of an unfavorable prognosis. According to the method, the determination of prognosis can be performed by comparing the measured LDL particle size and/or LDL subfraction concentration level to levels determined in comparable samples from healthy individuals or to levels known to corresponding with favorable or unfavorable outcomes. The absolute levels obtained may depend on an number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges. One of ordinary skill in the art is capable of performing a retrospective study that compares the determined LDL particle size and/or LDL subfraction concentration levels to the observed outcome of the patients and establishing ranges of levels that can be used to designate the prognosis of the patients with a particular disorder. For example, LDL particle size and/or LDL subfraction concentration levels in the lowest range would be indicative of a more favorable prognosis, while LDL particle size and/or LDL subfraction concentration levels in the highest ranges would be indicative of an unfavorable prognosis. Thus, in this aspect the term "elevated levels" refers to levels of LDL particle size and/or LDL subfraction concentration that are above the range of the reference value. In some embodiments patients with "high" or "elevated" LDL particle size and/or LDL subfraction concentration levels have levels that are higher than the median activity in a population of patients with that disease. In certain embodiments, "high" or "elevated" LDL particle size and/or LDL subfraction concentration levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of LDL particle size and/or LDL subfraction concentration in a test sample from a patient may relate to the prognosis of a patient in a continuous fashion, the determination of prognosis can be performed using statistical analyses to relate the determined levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses.

In certain embodiments, the prognosis of MHD patients can be correlated to the clinical outcome of the disease using the LDL particle size and/or LDL subfraction concentration level and other clinical factors. Simple algorithms have been described and are readily adapted to this end. The approach by Giles et. al., *British Journal of Hemotology*, 121:578-585, is exemplary. As in Giles et al., associations between categorical variables (e.g., LDL particle size and/or LDL subfraction concentration and clinical characteristics) can be assessed via crosstabulation and Fisher's exact test. Unadjusted survival probabilities can be estimated using the method of Kaplan and Meier. The Cox proportional hazards regression model also can be used to assess the ability of patient characteristics (such as LDL particle size and/or LDL subfraction concentration levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time in based on their LDL particle size and/or LDL subfraction concentration levels can be performed via the use of a visual basic for applications (VBA) computer program developed within Microsoft® Excel. The core construction and analysis may be based on the Cox proportional hazard models. The VBA application can be developed by obtaining a base hazard rate and parameter estimates. These statistical analyses can be performed using a statistical program such as the SAS® proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner.

In some embodiments of the invention, multiple prognostic factors, including LDL particle size and/or LDL subtraction concentration level, are considered when determining the prognosis of a patient. For example, the prognosis of a cancer patient may be determined based on LDL particle size and/or LDL subtraction concentration and one or more prognostic factors selected from the group consisting of status, age, gender and previous diagnosis. In certain embodiments, other prognostic factors may be combined with the LDL particle size and/or LDL subtraction concentration level in the algorithm to determine prognosis with greater accuracy.

MHD Prognosis Based on LDL Size

Disclosed herein are methods for predicting overall survival in a MHD patient based on LDL particle size analysis. Further disclosed herein are methods for monitoring the status of MHD patients based on LDL particle size analysis. In one embodiment, predicting the overall survival and monitoring the status of MHD patients requires a sample therefrom. The samples disclosed herein are represented by, but not limited to, whole blood, plasma, and/or serum. The present invention relates to methods for predicating overall survival and monitoring the status of MHD patients via comparing LDL particle size in a sample from a patient to a reference level or control population.

In one embodiment, a sample is obtained from a MHD patient. Subsequently, LDL particle size is measured in the sample by ion mobility analysis. In one embodiment, overall survival or mortality risk is then determined by comparing the patient's LDL particle size to a reference level or control population. In one embodiment, a difference between the patient's LDL particle size and the reference level indicates an increased risk of mortality.

In one embodiment, the LDL particle size of the reference level or the LDL particle size of a control population is between about 216-230 or between 216-224 Å. In one embodiment, the LDL particle size of the reference level or the LDL particle size of a control population is between about 216-222 Å, and preferably about 216 Å

In one embodiment, LDL particle size percentage difference between a MHD patient and the reference level or the control population is indicative of an increased risk of mortality, i.e., a decreased overall survival. In one embodiment, the percentage difference is a decrease of the MHD patient's LDL particle size compared to the reference level or control population. In one embodiment, the decrease in the MHD patient's LDL particle size compared to the reference level or control population is at least about 0.01, 0.1, 1, 2, 3, 4, 5, 6, 7, 8, 9, 10, 11, 12, 14, 15, 16, 17, 18, 19, 20, 30, 40, 50, 60, 70, 80, 90, or 100% decrease. In one embodiment, the decrease in the MHD patient's LDL particle size compared to the reference level or control population is at least about 1, 2, 3, 4, 5, 6, 7, 8, 9, or 10% decrease. In one embodiment, the decrease is at least about a 3% decrease in LDL particle size.

In one embodiment, LDL particle sizes equal to or less than about 230, 225, 224, 223, 222, 221, 220, 219, 218, 217, 216, or 215 Å, are indicative of an increased risk of mortality, i.e., a decreased overall survival. In one embodiment, LDL particle sizes equal to or less than about 220, 219, 218, 217, or 216 Å, are indicative of an increased risk of mortality. i.e. a decreased overall survival.

In one aspect, predicting, determining, assessing, or assessment, in the context of MHD overall survival, including, lipid-related health risks, cardiovascular conditions, and risk of cardiovascular diseases, refers to a statistical correlation of the resulting LDL particle size distribution with population mortality and risk factors, as well known in the art. In one embodiment, predicting, determining, assessing, or assessment, in the context of responsiveness to a therapeutic intervention, refers to comparison of the LDL particle size distribution before and after a therapeutic intervention is conducted.

MHD Prognosis Based on LDL Subfraction Concentration

Disclosed herein are methods for predicting overall survival in a MHD patient based on LDL subfraction concentration, i.e., very small LDL and/or large LDL concentration. Further disclosed herein are methods for monitoring the status of MHD patients based on LDL subfraction concentration, i.e., very small LDL and/or large LDL concentration. In one embodiment, predicting the overall survival and monitoring the status of MHD patients requires a sample therefrom. The samples disclosed herein are represented by, but not limited to, whole blood, plasma, and/or serum. The present invention relates to methods for predicating overall survival and monitoring the status of MHD patients by comparing LDL subtraction concentration, i.e., very small LDL and/or large LDL concentration, in a sample from a patient to a reference level or control population.

In one embodiment, a sample is obtained from a MHD patient. Subsequently, LDL subfraction concentration, i.e., very small LDL and/or large LDL concentration, is measured in the sample by ion mobility analysis. In one embodiment, overall survival or mortality risk is then determined by comparing the patient's LDL subfraction concentration, i.e., very small LDL and/or large LDL concentration, to a reference level or control population. In one embodiment, a difference between the patient's LDL subfraction concentration, i.e., very small LDL and/or large LDL concentration, and the reference level indicates an increased risk of mortality. In one embodiment, a difference between the patient's LDL subfraction concentration, i.e., very small LDL and/or large LDL concentration, and the reference level does not indicate an increased risk of mortality. In one embodiment, a difference between the patient's LDL subfraction concentration, i.e., very small LDL and/or large LDL concentration, and the reference level indicates an increased chance of overall survival.

In one embodiment, the very small LDL concentration of the reference level or the control population is equal to or between about 40-130, 50-125, or between 57-121 nmol/L.

In one embodiment, the very small LDL concentration of the reference level or the control population is equal to or between about 88-121 nmol/L. In one embodiment, the very small LDL concentration of the reference level or the control population is a concentration equal to or below about 100, 105, 110, 115, 120, 121, 125, 130, or 135 nmol/L.

In one embodiment, a very small LDL concentration of the MHD patient of at least about 110, 120, 130, 140, or 150 nmol/L, is indicative of an increased risk of mortality, i.e., a decreased overall survival. In one embodiment, a very small LDL concentration of the MHD patient of at least about 110, 111, 112, 113, 114, 115, 116, 117, 118, 119, 120, 121, 122, 125, 130, or 135 nmol/L, is indicative of an increased risk of mortality, i.e., a decreased overall survival. In one embodiment, a very small LDL concentration of the MHD patient greater than about 121 nmol/L is indicative of an increased risk of mortality, i.e., a decreased overall survival.

In one embodiment, the large LDL concentration of the reference level or the control population is equal to or between about 30-120, 40-110, or between about 44-105 nmol/L. In one embodiment, the large LDL concentration of the reference level or the control population is equal to or between about 77-105 nmol/L. In one embodiment, the large concentration of the reference level or the control population is a concentration equal to or below about 105 nmol/L.

In one embodiment, a large LDL concentration of the MHD patient of at least about 100, 110, 120, 130, 140, 150 nmol/L, is indicative of an increased overall survival. In one embodiment, a large LDL concentration of the MHD patient of at least about 100, 101, 102, 103, 105, or 106 nmol/L, is indicative of an increased overall survival. In one embodiment, a large LDL concentration of the MHD patient greater than about 105 nmol/L is indicative of an increased overall survival.

In one aspect, predicting, determining, assessing, or assessment, in the context of MHD overall survival, including, lipid-related health risks, cardiovascular conditions, and risk of cardiovascular diseases, refers to a statistical correlation of the resulting LDL subfraction concentration, i.e., very small LDL and/or large LDL concentration, with population mortality and risk factors, as well known in the art. In one embodiment, predicting, determining, assessing, or assessment, in the context of responsiveness to a therapeutic intervention, refers to comparison of the LDL subfraction concentration, i.e., very small LDL and/or large LDL concentration, before and after a therapeutic intervention is conducted.

In one aspect, the results of ion mobility LDL particle size, very small LDL concentration, and large LDL concentration, analyses are reported in an analysis report. In one embodiment, an analysis report is reported to a clinician, other health care provider, epidemiologist, and the like. In one embodiment, the analysis report includes the results of analysis of a sample from a MHD patient. In one embodiment, an analysis report may include biochemical characterization of the LDL particle sizes, very small LDL concentration, and/or large LDL concentration, in the sample, in addition to other sample characteristics known in the art, e.g., triglycerides, total cholesterol, LDL cholesterol, and/or HDL cholesterol, and the like. In one embodiment, an analysis report may include characterization of lipoproteins, and references ranges therefore, conducted on samples prepared by the methods provided herein. In one embodiment, an analysis report includes LDL size distribution obtained via ion mobility analysis. In one embodiment, an analysis report includes very small LDL concentration obtained via ion mobility analysis. In one embodiment, an analysis report includes large LDL concentration obtained via ion mobility analysis. In one embodiment, reference level or control population levels are included in the analysis report.

EXAMPLES

The present invention is further illustrated by the following examples, which should not be construed as limiting in any way. The present study examines which of the different aspects of conventional (triglycerides (TG) and cholesterol) and lipoprotein measurements (total particle concentrations (Pc) including HDL-Pc and LDL-Pc, LDL particle diameter [LDL-Pd] and subfraction-Pc) can better identify MHD patients with an increased death risk.

The examples described below illustrate methods for assessing risk hazard ratios using serological biomarkers. In MHD patients, traditional lipoprotein monitoring, such as measuring LDL levels, are not associated with cardiovascular events or mortality. However, direct determination of lipoprotein particle sizes and subfraction concentrations are possible via ion mobility analysis. Ion mobility analysis has been previously described in U.S. Pat. App. Pub. Nos. 2008/0305549 and 2008/0302666, and Otvos et al. (Clin. Chem. 54: 1307-1316, 2008). Ion mobility analysis provides for accurate and reproducible physical measurement of both the size and concentration of a broad range of circulating lipoproteins. Additionally, measuring the concentrations of diverse subfractions of lipoproteins elucidates a means for risk-stratification of multi-morbid individuals with chronic disease, e.g., MHD patients.

Lipoproteins were fractionated into very small, small, medium and large LDL subfractions from archived baseline plasma samples using an ion mobility method. This method uses an ion separation/particle detector system that fractionates lipoprotein particles from the small HDL particles to the large very low density lipoprotein (VLDL) particles and directly counts each lipoprotein particle to permit the determination of lipoprotein particle concentration. Assay characteristics for the ion mobility are as follows: inter-assay variation for LDL-Pd was <1.0% for higher concentration subfractions, HDL and LDL, the CV ranged from 13 to 20% and for lower concentration subfractions, IDL and VLDL, CVs were 17 to 30%. The diameter ranges used for each subfraction are as follows: HDL small, 76.5-105.0 Å HDL large, 105.0-145.0 Å; LDL very small, 180.0-208.2 Å; LDL small, 208.2-214.1 Å; LDL medium, 214.1-220.0 Å; LDL large, 220.0-233.3 Å; IDL 233.0-250.0 Å; IDL large, 250.0-296.0 Å; VLDL small, 296.0-335.0 Å; VLDL medium, 335.0-424.0 Å; and VLDL large, 424.0-520.0 Å. The ratio of large/small LDL-Pc was calculated using the concentrations of the two subfractions in the sizes listed above.

Example 1

Demographic, Clinical, and Laboratory Characterization of the Patient Population In the examples below, stored sera from a 235 MHD patient cohort was obtained and the 3- and 6-year survival rates were studied. The original patient cohort was derived over 5 years from a pool of over 3,000 MHD outpatients. Included were outpatients who underwent MHD treatment for at least 8 weeks, who were 18 years or older and who signed the Institutional Review Board approved consent form. Participants with an anticipated life expectancy <6 months (e.g. metastatic malignancy or advanced AIDS) were excluded. A total of 893 MUD patients provided informed consent to participate in the study. Approximately one-fourth of these patients (235 patients including 106 women) were randomly selected to undergo additional tests including lipid profile and body composition tests as described below.

Baseline demographic, clinical, and laboratory values in the 235 MHD patients according to gender and BMI are shown in Table 1. The patients' mean age (±SD) was 54 (±14) years; 45% of patients were women (n=106) and 26% (n=61) African-American. The median (interquartile range) of dialysis vintage was 44 (29-71) months. TG, TC and LDL-C were highest among women with high BMI and HDL-C was highest among women with low BMI.

TABLE 1

|  | Total | Women (n = 106) | | Men (n = 129) | | p-value |
| --- | --- | --- | --- | --- | --- | --- |
|  |  | BMI < 27 | BMI >= 27 | BMI < 27 | BMI >= 27 |  |
| N | 235 | 57 | 49 | 80 | 49 |  |
| Age (year) | 54 ± 14 | 57 ± 14 | 56 ± 15 | 51 ± 15 | 52 ± 13 | 0.06 |
| BMI (kg/m$^2$) | 27.4 ± 6.8 | 22.8 ± 2.6 | 33.5 ± 6.0 | 23.3 ± 2.1 | 33.5 ± 7.1 | <0.01 |
| African Americans (%) | 26 | 21 | 33 | 26 | 24 | 0.59 |
| Hispanic (%) | 52 | 54 | 45 | 49 | 61 | 0.37 |
| Diabetes mellitus (%) | 58 | 47 | 67 | 55 | 67 | 0.09 |
| Charlson comorbidity score | 1.8 ± 1.5 | 1.7 ± 1.3 | 1.8 ± 1.4 | 1.8 ± 1.5 | 2.3 ± 1.6 | 0.20 |
| Dialysis vintage (months) | 44(29-71) | 46(34-78) | 34(23-73) | 47(29-74) | 39(26-63) | 0.21 |
| Body fat (%) via NIR | 45.0 ± 29.3 | 36.5 ± 25.9 | 75.6 ± 25.9 | 23.8 ± 10.7 | 58.6 ± 33.3 | <0.01 |
| Dialysis dose, Kt/V (sp) | 1.67 ± 0.31 | 1.79 ± 0.30 | 1.70 ± 0.34 | 1.62 ± 0.29 | 1.56 ± 0.25 | <0.01 |
| Serum albumin (mg/dl) | 4.05 ± 0.45 | 3.92 ± 0.41 | 3.94 ± 0.32 | 4.15 ± 0.40 | 4.04 ± 0.31 | <0.01 |
| creatinine (mg/dl) | 9.7 ± 2.8 | 9.0 ± 2.7 | 8.9 ± 2.0 | 10.3 ± 3.0 | 10.4 ± 2.9 | <0.01 |
| CRP (mg/dl) | 3.5(1.7-6.7) | 2.2(1.1-5.0) | 4.7(2.7-7.3) | 2.9(1.3-5.8) | 4.7(2.7-7.8) | <0.01 |
| IL-6(mg/dl) | 6.0(3.8-12.0) | 4.9(3.4-11.4) | 8.0(4.4-10.9) | 5.9(3.4-12.9) | 7.3(4.2-12.8) | 0.32 |
| TNF-a (mg/dl) | 3.5(2.4-4.6) | 3.5(1.9-4.6) | 3.7(2.1-4.5) | 3.5(2.6-4.4) | 3.5(2.5-5.1) | 0.86 |
| Conventional lipid measurements |  |  |  |  |  |  |
| triglyceride (mg/dl) | 153 ± 11 | 118 ± 52 | 196 ± 113 | 133 ± 86 | 180 ± 160 | <0.01 |
| total cholesterol (mg/dl) | 143 ± 42 | 135 ± 37 | 166 ± 50 | 133 ± 34 | 146 ± 42 | <0.01 |
| LDL-C (mg/dL) | 76 ± 29 | 68 ± 26 | 88 ± 29 | 72 ± 28 | 80 ± 32 | <0.01 |
| HDL-C (mg/dL) | 37 ± 12 | 43 ± 15 | 37 ± 14 | 36 ± 10 | 32 ± 9 | <0.01 |
| Alternative LDL particle measures |  |  |  |  |  |  |
| total LDL-Pc (nmol/L) | 255 ± 154 | 215 ± 156 | 299 ± 171 | 241 ± 149 | 281 ± 162 | 0.02 |
| very small LDL-Pc (nmol/L) | 101 ± 66 | 87 ± 46 | 119 ± 78 | 95 ± 63 | 111 ± 73 | 0.04 |
| small LDL-Pc (nmol/L) | 30 ± 22 | 23 ± 13 | 38 ± 29 | 27 ± 17 | 37 ± 27 | <0.01 |
| medium LDL-Pc (nmol/L) | 34 ± 25 | 27 ± 19 | 42 ± 30 | 32 ± 23 | 40 ± 27 | <0.01 |
| large LDL-Pc (nmol/L) | 89 ± 64 | 79 ± 65 | 100 ± 69 | 87 ± 62 | 94 ± 57 | 0.34 |
| LDL-Pd (angstrom) | 215 ± 10 | 217 ± 10 | 213 ± 10 | 217 ± 10 | 214 ± 10 | 0.06 |
| Alternative HDL particle measures |  |  |  |  |  |  |
| total HDL-Pc (nmol/L) | 2773 ± 3500 | 2921 ± 3805 | 2324 ± 1873 | 3038 ± 4084 | 2616 ± 3387 | 0.69 |
| small HDL-Pc (nmol/L) | 2228 ± 3309 | 2328 ± 3575 | 1777 ± 1768 | 2511 ± 3852 | 2101 ± 3252 | 0.66 |
| large HDL-Pc (nmol/L) | 566 ± 399 | 603 ± 426 | 547 ± 377 | 583 ± 432 | 514 ± 331 | 0.66 |

All values are presented as mean ± SD or percentages except for variables that are not normally distributed (vintage, CRP, IL6 and TNF alpha) which we used interquartile range(IQR).

All analysis are ANOVA except for variables that are not normally distributed (vintage, CRP, IL6 and TNF alpha) which we used Kruskal-Wallis test.

Abbreviations:

LDL, Low density lipoprotein;

LDL-C, LDL cholesterol;

LDL-Pc, LDL particle concentration;

LDL-Pd, LDL particle diameter;

HDL, high density lipoprotein;

HDL-C, HDL cholesterol;;

TG, triglyceride;

CRP, C-reactive protein;

IL-6, interleukin-6;

TNF-a, tumor necrosis factor-alpha;

BMI, body mass index.

Example 2

Correlation of Lipid Fractions and Other Physiological Variables

Table 2 shows the correlation coefficients of relevant measures with the subfractions of LDL-Pc and HDL-Pc. The four conventional lipid measures, serum TC, LDL-C, HDL-C and TG, were correlated with all subfractions of LDL-Pc. HDL-C was associated negatively with small and medium LDL-Pc and positively with large HDL-Pc. LDL-Pd was correlated positively with very small and large LDL-Pc and negatively with small HDL-Pc. Scatter plots of correlations of conventional serum LDL-C and HDL-C with alternative large LDL-Pc and large HDL-Pc concentrations indicated correlation coefficients of r=0.34 (p<0.01) and r=0.23 (p<0.01), respectively (FIG. 1).

TABLE 2

| | LDL particle measures | | | | HDL particle measures | |
|---|---|---|---|---|---|---|
| | Very small LDL-Pc | Small LDL-Pc | Medium LDL-Pc | Large LDL-Pc | Small HDL-Pc | Large HDL-Pc |
| Age | 0.05 | −0.04 | 0.02 | −0.01 | −0.17* | 0.08 |
| Vintage | −0.11 | −0.13* | −0.11 | −0.10 | 0.05 | −0.06 |
| Charlson comorbidity score | 0.01 | −0.02 | 0.01 | 0.02 | 0.05 | 0.00 |
| BMI | 0.18** | 0.17** | 0.16* | 0.08 | 0.00 | −0.02 |
| NIR Fat mass percent | 0.21** | 0.09 | 0.07 | 0.03 | 0.01 | 0.00 |
| TG | 0.39** | 0.43** | 0.43** | 0.33** | 0.15 | 0.01 |
| TC | 0.33* | 0.36** | 0.38** | 0.37** | 0.09 | 0.01 |
| LDL-C | 0.21** | 0.28** | 0.29** | 0.33** | 0.04 | −0.06 |
| HDL-C | −0.07 | −0.23** | −0.21** | −0.15* | −0.07 | 0.14* |
| Total LDL-Pc | 0.87** | 0.96** | 0.93** | 0.89** | 0.34** | 0.35** |
| Very small LDL-Pc | — | 0.87** | 0.77** | 0.66** | 0.41** | 0.33** |
| Small LDL-Pc | 0.87** | — | 0.95** | 0.84** | 0.35* | 0.25** |
| Medium LDL-Pc | 0.77** | 0.95** | — | 0.93** | 0.27** | 0.24** |
| Large LDL-Pc | 0.66** | 0.84** | 0.93** | — | 0.25** | 0.29** |
| Total HDL-Pc | 0.55** | 0.29** | 0.21** | 0.17* | 0.85** | 0.52** |
| Small HDL-Pc | 0.41* | 0.35** | 0.27** | 0.01 | — | 0.11 |
| Large HDL-Pc | 0.33** | 0.25** | 0.24** | 0.25** | 0.11 | — |
| LDL-Pd | 0.31** | −0.11 | −0.02 | 0.29** | −0.20** | −0.09 |
| CRP | −0.01 | 0.00 | 0.00 | −0.06 | −0.01 | −0.09 |
| IL-6 | −0.11 | −0.12 | −0.15* | −0.14* | 0.00 | 0.00 |
| TNF-a | −0.06 | −0.06 | −0.04 | −0.03 | 0.02 | −0.17** |
| Dietary data | | | | | | |
| Energy intake | 0.03 | 0.00 | −0.06 | −0.09 | −0.16 | 0.04 |
| SAFA intake | 0.04 | 0.02 | −0.07 | −0.10 | −0.15 | 0.07 |
| MUFA intake | −0.02 | −0.01 | −0.09 | −0.12 | −0.11 | 0.01 |
| PUFA intake | −0.10 | −0.13 | −0.20 | −0.19 | −0.13 | −0.03 |
| SGA | −0.12 | −0.16* | −0.15* | −0.12 | −0.03 | −0.02 |

*p < 0.05,
**p < 0.01 (r values >=0.20 are bold)

Example 3

Correlation of Lipid Fractions with Mortality

Over the six years of the cohort 71 MHD patients (31%) died. The death hazard ratio (HR) across the quartiles of conventionally measured serum LDL-C and HDL-C and alternative LDL-Pound HDL-Pc was calculated. As shown in Table 3 no association was observed between LDL-C, HDL-C or LDL-Pc and mortality in MHD patients. However, the highest quartile of the total HDL-Pc was associated with 2.2-fold higher death risk. Very low density lipoprotein (VLDL) and intermediate density lipoprotein (IDL) cholesterol concentrations were not associated with increased or decreased mortality either (data not shown).

The mortality-predictabilities of alternative lipid-Pc and LDL-Pd measures were examined by calculating the death hazard ratio (HR) across their quartiles, highest vs. lowest. Among these subfractions of LDL-P, the highest concentrations of very small and large LDL-P were associated with highest and lowest mortality, respectively, especially after adjustment for case-mix, conventional lipids, MICS and inflammation (Table 4). No association was observed between alternative small and large HDL-Pc and mortality (Table 2).

Figure 2:
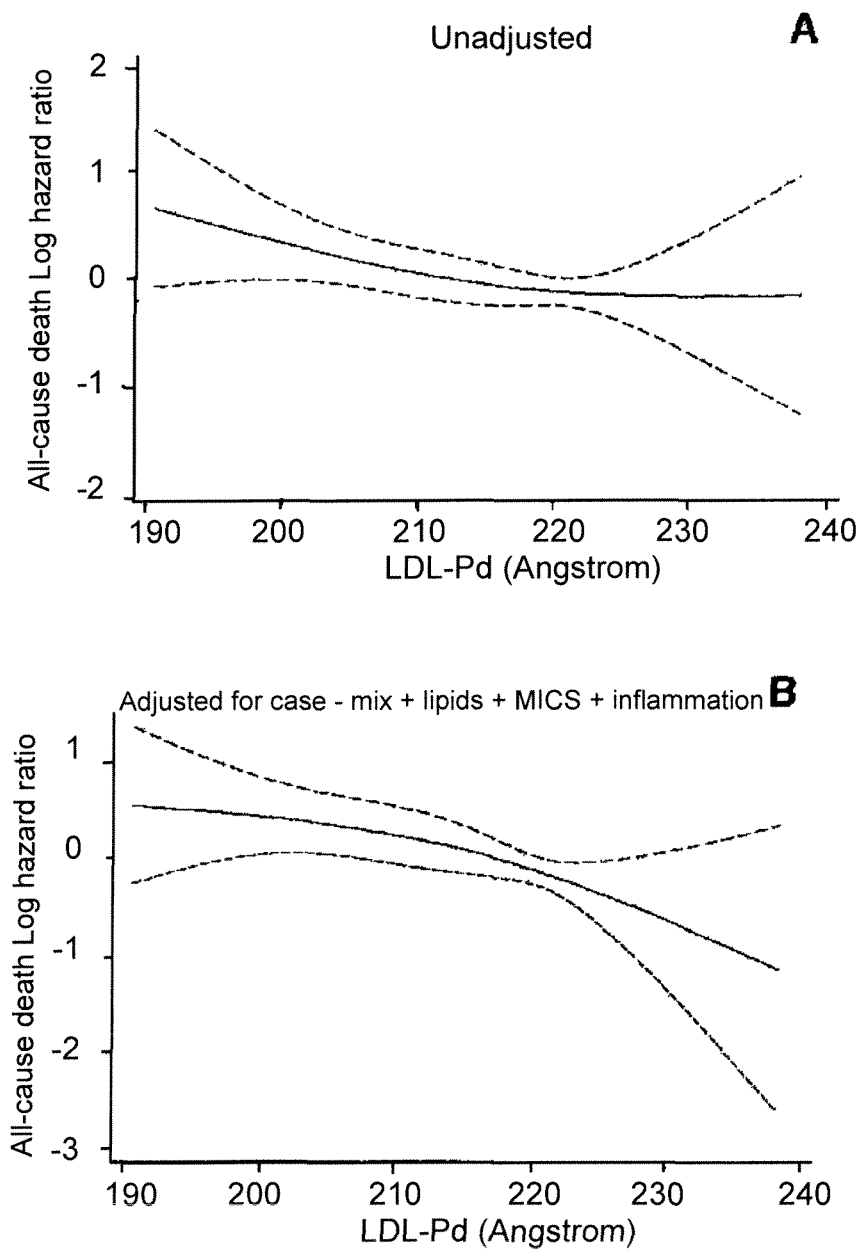
FIG. 2 is a series of cubic spline models of the Cox proportional regression analyses reflecting adjusted mortality-predictability (with 95% CI) according to the LDL-P diameter in the entire cohort of 235 maintenance MHD patients over 5 years (from October 2001 to January 2007), as discussed in Example 3, Spline models are with 2 degrees of freedom.

The death HRs were also calculated for the quartiles of LDL-Pd (Table 6) and large/small LDL-Pc ratio (Table 2). There was no significant association in the unadjusted models. However, both measures were associated with decreased mortality after adjustment for case-mix, conventional lipids, MICS and inflammation. The death HRs (1st to 4th quartiles) for quartiles of LDL-Pd were 1.0, 0.93 (0.46-1.87), 0.43 (0.21-0.89), and 0.45 (0.31-1.00); and for quartiles of the large/small LDL-Pc ratio 1.0, 0.64 (0.31-1.32), 0.51 (0.25-1.02), and 0.43 (0.20-0.95), respectively (Table 5). These relationships were verified in cubic spline analyses examining Cox based multivariate adjusted association between smaller LDL-Pd and higher mortality (FIG. 2). Hence, in Cox based multivariate adjusted analysis smaller LDL-Pd was associated with higher mortality. The net reclassification improvement for LDL particle diameter, very small and large LDL was calculated and found to be 0.05 (p=0.25), 0.22 (p<0.01) and 0.03 (p=0.47), respectively.

TABLE 3

| Conventional LDL | Q1 (n = 62) | Q2 (n = 58) | Q3 (n = 59) | Q4 (n = 56) | P-for-trend |
|---|---|---|---|---|---|
| LDL-C (mg/dl) | <55 | 55-72 | 73-94 | >94 | |
| Unadjusted | 1 | 1.25(0.66-2.37) | 0.88(0.44-1.78) | 1.16(0.61-2.20) | 0.90 |
| Case-mix[1] + lipids[2] | 1 | 1.11(0.56-2.19) | 0.98(0.47-2.05) | 1.21(0.58-2.50) | 0.71 |
| Previous + MICS[3]+ inflammation[4] | 1 | 1.41(0.68-2.89) | 1.16(0.52-2.58) | 1.43(0.65-1.15) | 0.49 |

| Conventional HDL | Q1 (n = 64) | Q2 (n = 55) | Q3 (n = 62) | Q4 (n = 54) | |
|---|---|---|---|---|---|
| HDL-C (mg/dl) | <29 | 29-34 | 35-44 | >44 | |
| Unadjusted | 1 | 0.95(0.48-1.92) | 1.10(0.58-2.13) | 1.52(0.80-2.91) | 0.19 |
| Case-mix + lipids | 1 | 0.77(0.37-1.62) | 0.92(0.44-1.90) | 0.85(0.40-1.81) | 0.80 |
| Previous + MICS+ inflammation | 1 | 0.92(0.41-2.02) | 1.19(0.52-2.74) | 0.99(0.43-2.23) | 0.93 |

| Alternative LDL particle | Q1 (n = 60) | Q2 (n = 59) | Q3 (n = 58) | Q4 (n = 58) | p-for-trend |
|---|---|---|---|---|---|
| Total LDL-Pc (nmol/L) | <144 | 144-215 | 216-315 | >315 | |
| Unadjusted | 1 | 0.89(0.46-1.73) | 0.93(0.47-1.82) | 0.87(0.45-1.69) | 0.72 |
| Case-mix + lipids | 1 | 0.76(0.37-1.55) | 1.29(0.61-2.73) | 1.04(0.48-2.27) | 0.60 |
| Previous + MICS+ inflammation | 1 | 0.46(0.20-1.04) | 1.36(0.62-2.98) | 0.84(0.35-2.03) | 0.65 |

| Alternative HDL particle | Q1 (n = 59) | Q2 (n = 59) | Q3 (n = 59) | Q4 (n = 58) | |
|---|---|---|---|---|---|
| Total HDL-Pc (nmol/L) | <936 | 936-1466 | 1467-2919 | >2919 | |
| Unadjusted | 1 | 0.86(0.42-1.77) | 1.03(0.52-2.08) | 1.50(0.78-2.87) | 0.18 |
| Case-mix + lipids | 1 | 1.00(0.47-2.11) | 1.58(0.76-3.27) | 1.69(0.86-3.32) | 0.07 |
| Previous + MICS+ inflammation | 1 | 1.05(0.48-2.29) | 1.44 (0.67-3.11) | 2.22(1.02-4.81)* | 0.03 |

[1]Case-mix included age, gender, race/ethnicity, diabetes mellitus, dialysis vintage, modified Charlson comorbidity score and dialysis dose (single pool Kt/V).
[2]Lipids included total LDL and HDL particles concentrations and triglyceride.
[3]Malnutrition-inflammation complex syndrome (MICS) variables included serum or blood levels of phosphorus, albumin, creatinine, calcium, ferritin, hemoglobin, normalized protein catabolic rate (nPCR), also known as normalized protein nitrogen appearance (nPNA); and body mass index.
[4]Inflammatory markers include serum concentrations of C-reactive protein, interleukin-6, and tumor necrosis factor-α.
*Significant values are in bold (p < 0.05)
**P for interaction pertains to malnutrition-inflammation complex was not significant in any of the models (>0.19), >0.33 and >0.10 for conventional LDL, conventional HDL, alternative LDL and alternative HDL particle models respectively)
Death hazard ratios are provided as mean values with 95% confidence intervals
Abbreviations:
LDL, Low density lipoprotein;
LDL-C, LDL cholesterol;
LDL-Pc LDL particle concentration;
HDL, high density lipoprotein;
HDL-C, HDL cholesterol.

TABLE 4

| Very small LDL-P | Q1 (n = 58) | Q2 (n = 60) | Q3 (n = 59) | Q4 (n = 58) | P-for-trend |
|---|---|---|---|---|---|
| Very small LDL-Pc (nmol/L) | <57 | 57-87 | 88-121 | >121 | |
| Unadjusted | 1 | 0.84(0.42-1.70) | 0.93(0.45-1.91) | 1.54(0.82-2.89) | 0.13 |
| Case-mix[1] + lipids[2] | 1 | 0.90(0.43-1.90) | 1.18(0.53-2.59) | 2.44(1.10-5.44)* | 0.02 |
| Previous + MICS[3]+ inflammation[4] | 1 | 0.67(0.29-1.55) | 0.88(0.38-2.05) | 2.43 (1.03-5.72)* | 0.03 |

| Small LDL-P | Q1 (n = 62) | Q2 (n = 60) | Q3 (n = 59) | Q4 (n = 54) | |
|---|---|---|---|---|---|
| Small LDL-Pc (nmol/L) | <15 | 15-24 | 25-36 | >36 | |
| Unadjusted | 1 | 1.57(0.83-2.97) | 1.68(0.56-2.34) | 0.92(0.45-1.89) | 0.63 |
| Case-mix + lipids | 1 | 1.60(0.84-3.06) | 1.43(0.69-2.93) | 1.40(0.61-3.19) | 0.43 |
| Previous + MICS+ inflammation | 1 | 1.36(0.67-2.73) | 1.73(0.82-3.61) | 1.23(0.49-3.12) | 0.41 |

| Medium LDL-P | Q1 (n = 64) | Q2 (n = 55) | Q3 (n = 57) | Q4 (n = 59) | |
|---|---|---|---|---|---|

TABLE 4-continued

| | | | | | |
|---|---|---|---|---|---|
| Medium LDL-Pc (nmol/L) | <17 | 47-26 | 27-46 | >46 | |
| Unadjusted | 1 | 1.42(0.74-2.72) | 1.32(0.67-2.58) | 0.87(0.43-1.78) | 0.65 |
| Case-mix + lipids | 1 | 1.50(0.76-2.97) | 1.64(0.80-3.33) | 1.17(0.51-2.68) | 0.60 |
| Previous + MICS[+] inflammation | 1 | 1.24(0.60-2.58) | 2.07(0.98-4.37) | 1.15(0.46-2.91) | 0.37 |

| Large LDL-P | Q1 (n = 63) | Q2 (n = 55) | Q3 (n = 59) | Q4 (n = 58) | |
|---|---|---|---|---|---|
| Large LDL-Pc (nmol/L) | <44 | 44-76 | 77-105 | >105 | |
| Unadjusted | 1 | 0.70(0.37-1.34) | 0.88(0.47-1.62) | 0.45(0.22-0.92)* | 0.05 |
| Case-mix + lipids | 1 | 0.63(0.31-1.28) | 0.68(0.34-1.37) | 0.37(0.16-0.87)* | 0.04 |
| Previous + MICS[+] inflammation | 1 | 0.51(0.23-1.12) | 0.96(0.45-2.05) | 0.38(0.15-0.96)* | 0.13 |

[1]Case-mix included age, gender, race/ethnicity, diabetes mellitus, dialysis vintage, modified Charlson comorbidity score and dialysis dose (single pool Kt/V).

[2]Lipids included LDL and HDL cholesterol concentrations and triglyceride plus large LDL and very small LDL in the analysis of quartiles of very small LDL and large LDL respectively.

[3]Malnutrition-inflammation complex syndrome (MICS) variables included serum or blood levels of phosphorus, albumin, creatinine, calcium, ferritin, hemoglobin, normalized protein catabolic rate (nPCR), also known as normalized protein nitrogen appearance (nPNA); and body mass index.

[4]Inflammatory markers include serum concentrations of C-reactive protein, interleukin-6, and tumor necrosis factor-α.

*Significant values are in bold ($p < 0.05$)

**P for interaction pertains to malnutrition-inflammation complex was not significant in any of the models (see text)

Death hazard ratios are provided as mean values with 95% confidence intervals

Abbreviations:

LDL, Low density lipoprotein;

LDL-Pc, LDL particle concentration.

TABLE 5

| Small HDL-P | Q1 (n = 59) | Q2 (n = 60) | Q3 (n = 58) | Q4 (n = 58) | P-for-trend | P for interaction** |
|---|---|---|---|---|---|---|
| Small HDL-Pc (nmol/L) | <494 | 494-1069 | 1070-2538 | >2538 | | |
| Unadjusted | 1 | 071(0.34-1.45) | 1.09(0.56-2.14) | 1.28(0.67-2.45) | 0.17 | 0.51 |
| Case-mix1 | 1 | 0.78(0.38-1.62) | 1.38(0.70-2.73) | 1.34(0.70-2.58) | 0.09 | 0.57 |
| Case-mix + lipids2 | 1 | 0.70(0.33-1.46) | 1.39(0.69-2.79) | 1.36(0.69-2.66) | 0.15 | 0.33 |
| Previous + MICS3 | 1 | 0.66(0.31-1.41) | 1.04(0.50-2.17) | 1.58(0.77-3.27) | 0.13 | 0.58 |
| Previous + inflammation4 | 1 | 0.64(0.30-1.37) | 1.00(0.48-2.10) | 1.54(0.74-3.21) | 0.15 | 0.58 |

| Large HDL-P | Q1 (n = 59) | Q2 (n = 59) | Q3 (n = 58) | Q4 (n = 59) | | |
|---|---|---|---|---|---|---|
| Large HDL-Pc (nmol/L) | <304 | 304-473 | 474-685 | >685 | | |
| Unadjusted | 1 | 1.21(0.57-2.54) | 1.69(0.84-3.40) | 1.92(0.97-3.80) | 0.03 | 0.78 |
| Case-mix1 | 1 | 1.38(0.66-2.95) | 1.73(0.85-3.52) | 1.83(0.92-3.67) | 0.79 | 0.90 |
| Case-mix + lipids2 | 1 | 1.28(0.69-2.79) | 1.49(0.73-3.06) | 1.24(0.56-2.70) | 0.64 | 0.99 |
| Previous + MICS3 | 1 | 1.59(0.70-3.61) | 1.59(0.74-3.44) | 1.40(0.51-3.21) | 0.66 | 0.85 |
| Previous + inflammation4 | 1 | 1.66(0.76-3.79) | 1.55(0.71-3.73) | 1.42(0.62-3.27) | 0.66 | 0.83 |

| Large/small LDL-P ratio5 | Q1 (n = 59) | Q2 (n = 59) | Q3 (n = 59) | Q4 (n = 58) | | |
|---|---|---|---|---|---|---|
| Large/small LDL-Pc | <0.44 | 0.44-0.68 | 0.69-0.97 | >0.97 | | |
| Unadjusted | 1 | 0.59(0.31-1.13) | 0.63(0.34-1.19) | 0.62(0.33-1.17) | 0.17 | 0.83 |
| Case-mix1 | 1 | 0.52(0.27-1.01) | 0.63(0.33-1.18) | 0.48(0.24-0.97)* | 0.06 | 0.94 |
| Case-mix + lipids2 | 1 | 0.46(0.23-0.92) | 0.52(0.27-1.00)* | 0.41(0.20-0.87)* | 0.03 | 0.89 |
| Previous + MICS3 | 1 | 0.63(0.31-1.28) | 0.52(0.26-1.05) | 0.43(0.20-0.93)* | 0.02 | 0.83 |

TABLE 5-continued

| | | | | | | |
|---|---|---|---|---|---|---|
| Previous + inflammation[4] | 1 | 0.64(0.31-1.32) | 0.51(0.25-1.02) | 0.43(0.20-0.95)* | 0.02 | 0.87 |

[1]Case-mix included age, gender, race/ethnicity, diabetes mellitus, dialysis vintage, modified Charlson comorbidity score and dialysis dose (single pool Kt/V).
[2]Lipids included LDL and HDL cholesterol concentrations and triglyceride.
[3]Malnutrition-inflammation complex syndrome (MICS) variables included serum or blood levels of phosphorus, albumin, creatinine, calcium, ferritin, hemoglobin, normalized protein cataboiic rate (nPCR), also known as normalized protein nitrogen appearance (nPNA); and body mass index.
[4]Inflammatory markers include serum concentrations of C-reactive protein, interleukin-6, and tumor necrosis factor-α.
[5]The cutoffs for the quartiles of the large/small LDL-Pc ratio were 0.11-0.44, 0.45-0.68, 0.69-0.96 and 0.97-1.74 for Quartiles 1 to 4, respectively.
Death hazard ratios are provided as mean values with 95% confidence intervals
*Significant values are in bold ($p < 0.05$)
**P for interaction pertains to malnutrition-inflammation complex
Abbreviations:
LDL, Low density lipoprotein;
LDL-Pc, LDL particle concentration;;
HDL-Pc; HDL particle concentration

TABLE 6

| LDL particle diameter (LDL-Pd) quartiles | Q1 (n = 61) | Q2 (n = 57) | Q3 (n = 59) | Q4 (n = 58) | P-for-trend |
|---|---|---|---|---|---|
| LDL particle diameter (Å) | <211.4 | 211.4-216.4 | 216.5-222.1 | >222.8 | |
| Unadjusted | 1 | 0.76(0.40-1.43) | 0.65(0.34-1.23) | 0.70(0.37-1.33) | 0.22 |
| Case-mix[1] + lipids[2] | 1 | 0.97(0.50-1.86) | 0.49(0.25-0.96)* | 0.52(0.25-1.09) | 0.03 |
| Previous + MICS[3] + inflammation[4] | 1 | 0.93(0.46-1.87) | 0.43(0.21-0.89)* | 0.45(0.31-1.00)* | 0.02 |

[1]Case-mix included age, gender, race/ethnicity, diabetes mellitus, dialysis vintage, modified Charlson comorbidity score and dialysis dose (single pool Kt/V).
[2]Lipids included LDL and HDL cholesterol concentrations and triglyceride
[3]Malnutrition-inflammation complex syndrome (MICS) variables included serum or blood levels of phosphorus, albumin, creatinine, calcium, ferritin, hemoglobin, normalized protein catabolic rate (nPCR), also known as normalized protein nitrogen appearance (nPNA); and body mass index.
[4]Inflammatory markers include serum concentrations of C-reactive protein, interleukin-6, and tumor necrosis factor-α.
Death hazard ratios are provided as mean values with 95% confidence intervals
*Significant values are in bold ($p < 0.05$)

Example 4

Risk Stratification of MHD Patients Using Alternate Lipid Measurements

Figure 3:
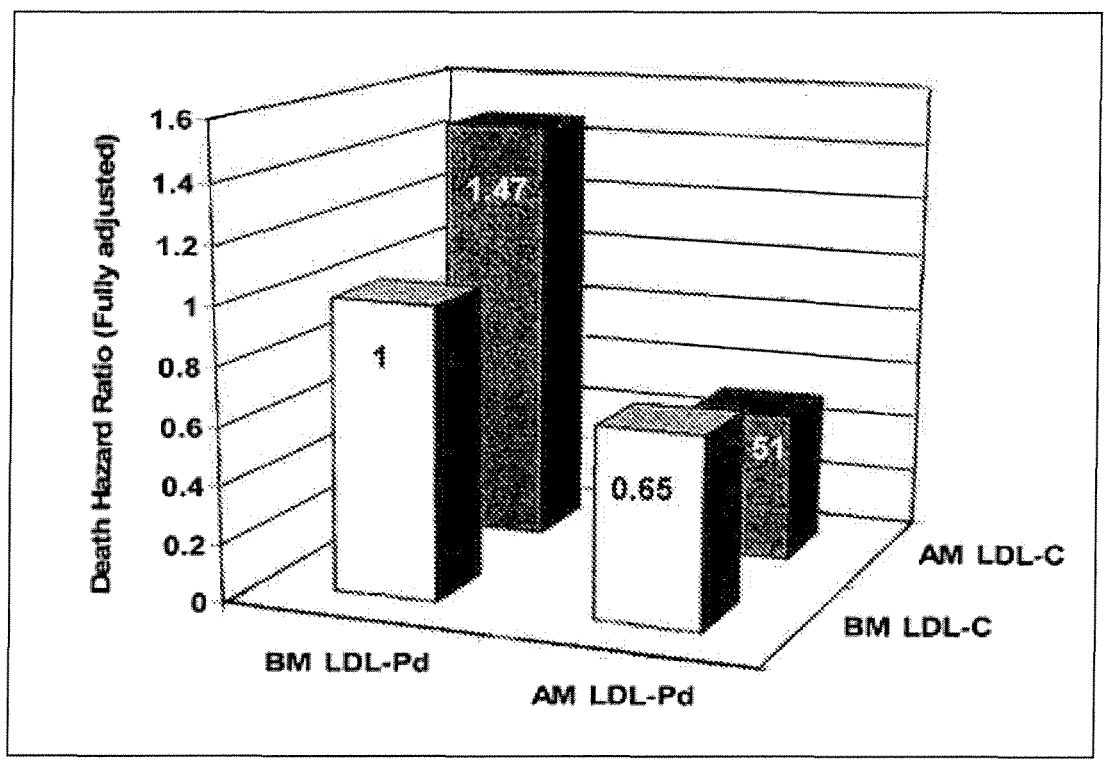
FIG. 3 is a bar graph showing the death hazard ratio according to categories (above median (AM) or below median (BM)) of LDL-C and LDL-P diameter after full adjustment. Median values for LDL-C and LDL-Pd are 73 mg/dL and 216.5 A, respectively. Full adjustment means adjustment for case-mix (age, gender, race/ethnicity, diabetes mellitus, dialysis vintage, modified Charlson comorbidity score and dialysis dose (single pool Kt/V)) and lipids (TG, LDL and HDL particle concentration), MICS (serum or blood levels of phosphorus, albumin. creatinine, calcium, ferritin, hemoglobin, normalized protein catabolic rate (nPCR), also known as normalized protein nitrogen appearance (nPNA); and body mass index) and inflammation (CRP, IL6, TNF-α).
Figure 4:
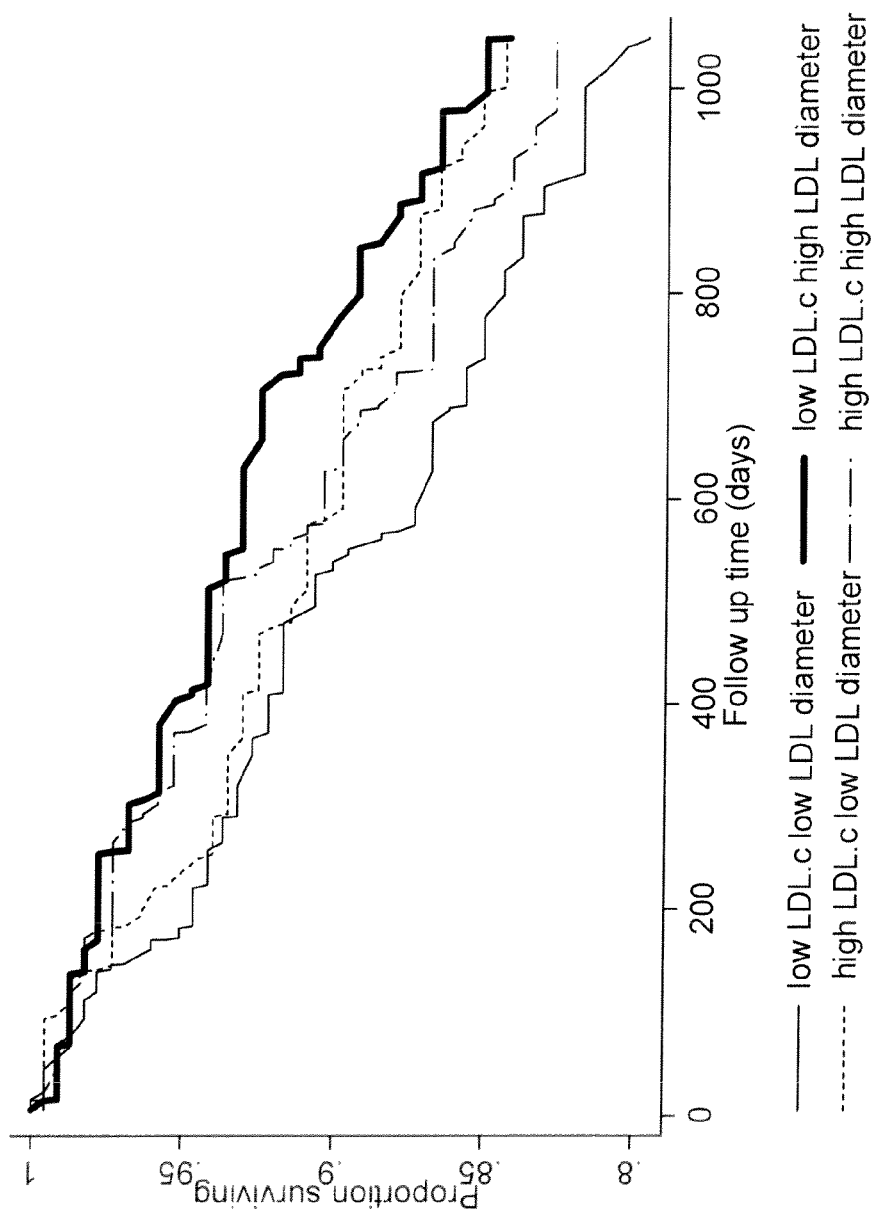
FIG. 4 is a line graph showing the Kaplan-Meier proportion of surviving MHD patients after 5 years of observation according to the categories of LDL cholesterol concentration and LDL particle diameter in 235 MHD patients.

In order to investigate whether the alternative lipid measures described herein can help better risk-stratify MHD patients, we examined the mortality predictability of the combinations of LDL-Pd with conventional LDL-C by dichotomizing all subjects into below-median vs. above-median LDL-C (median: 73 mg/dL) as well as below-median vs. above-median LDL-Pd (median: 216.5 Å), leading to four (2×2) mutually exclusive groups. As shown in FIG. 3, above-median LDL-C combined with above-median LDL-Pd was associated with the lowest death risk. FIG. 3 illustrates the statistical interactions, in that above-median vs. below-median serum LDL-C appeared paradoxically protective in the context of above-median LDL-Pd but within the below-median LDL-Pd, above-median serum LDL-C was associated with a trend towards a 47% higher death risk. FIG. 4 shows the Kaplan-Meier proportion of surviving according to the four aforementioned categories of LDL-Pd and LDL-C concentration, which were consistent with the Cox models. We also implemented the same 2×2 approach to examine the mortality-predictability of the four combinations of total LDL-Pc and LDL-Pd by dichotomizing each into above-median versus below-median. Median value for total LDL-Pc=216 nmol/L. We also calculated death hazard ratios of conventional LDL-C, HDL-C and alternative total LDL-P concentrations across above-median and below-median values of alternative LDL-P diameter, in that median values were used to dichotomize each measure forming a 2-by-2 table. After multivariate adjustments above-median total LDL-Pc combined with above-median LDL-Pd was associated with the lowest death risk, i.e. 74% lower mortality compared to below-median total LDL-Pc combined with below-median LDL-Pd. However, p-values-for-interaction with LDL-Pd were not significant (>0.17).

Summary of Results and Discussion

We examined the mortality predictability of both traditional and alternative measures of lipoproteins and their particle and subfraction concentrations, including LDL-Pd, in a cohort of 235 MHD patients who were followed for up to 6 years. It was discovered that non-traditional lipoprotein measures could better predict outcomes of MHD patients. Prior studies have indicated a lipid paradox in dialysis patients, in that lower serum TC and LDL-C are paradoxically associated with higher death risk. Hence, alternative lipoprotein measures may more accurately reflect the increased cardiovascular risk in this patient population.

The present studies demonstrate that conventional TC, LDL-C and HDL-C were not able to predict mortality, consistent with the previous literature in CKD and CHF patient population. Higher HDL-Pc was associated with higher death risk. Prognostic factors for survival in these patients included LDL-P subfraction concentrations and LDL-Pd. Decreased LDL-Pd, indicating smaller LDL particle size, was associated with an increased death risk even after adjustment for demographics, comorbidities, and conventional measurements of lipids, nutritional status and inflammation. Higher concentrations of very small LDL-P were associated with higher mortality, whereas higher concentrations of large LDL-P were associated with greater survival. The present studies also demonstrate that larger (above-median) LDL-Pd with either above-median or below-median total LDL-Pc was associated with greater survival. In patients with below-median LDL-Pd, the highest risk of mortality was associated with above-median levels of LDL-C. However, above-median LDL-Pc combined with below-median LDL-Pd had a lower risk of mortality than below-median LDL-Pd and below-median LDL-Pc. There is a strong trend in patients with below-median LDL-Pd, above-median LDL-C and above-median LDL-Pc showing increased and decreased risk, respectively. This indicates that the LDL-C content of the LDL particles this population may not be proportional to the LDL-Pd. It is generally assumed that larger the LDL particles contain more cholesterol. However, the present data indicates a difference in particle composition in dialysis patients. It was also found that larger LDL-Pd with either above-median or below-median total HDL-C tended to correlate with greater survival.

Conventional chemical measures of lipid concentration have long been the most used clinical measurements of lipid profile. However, in chronic disease states such as CKD and CHF these measures do not appear to predict outcomes. Total LDL-Pc and LDL-Pd show better correlation with atherosclerotic progression and cardiovascular events than conventional LDL-C. Indeed, conventional LDL-C can be low, yet total LDL-Pc may be high and cardiovascular events rates may be increased. Conversely, conventional LDL-C can be high, yet total LDL-Pc low especially in the setting of low cardiovascular risk. These scenarios are more likely to be the case in chronic disease states such as CKD and CHF where conventional lipid concentrations may be confounded by wasting syndrome and MICS.

Conventional lipids measurements such as LDL-C and HDL-C have not proven to be of great assistance in MHD patients in assessing cardiovascular or death risk. This was also observed in the present study in which the measurement of LDL-Pd and LDL-P subtraction concentration better identified MHD individuals at increased risk of death for up to 6 years thereafter. The association of LDL-Pd and its subfraction concentrations with death was independent of conventional LDL-C and HDL-C or inflammation. In the present study, adjustments for case-mix and lipids as well as MICS increased the robustness of the ion mobility measured alternative LDL parameter for predicting mortality demonstrating that the LDL-Pd and subfraction concentrations are superior predictors of mortality independent of conventional lipid measurements.

The present invention is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language including, but not limited to, e.g., "up to," "at least," "greater than," "less than," and the like include the number recited and refer to ranges which can be subsequently broken down into subranges as discussed above. Finally, as will be understood by one skilled in the art, a range includes each individual member.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for predicting mortality risk in a maintenance hemodialysis (MHD) patient comprising:
   a. separating lipoprotein particles from non-lipoprotein particles in a plasma sample from an MHD patient;
   b. irradiating with alpha radiation and fractionating the lipoprotein particles according to particle diameter using on mobility lipoprotein fractionation;
   c. determining a very small low density lipoprotein (vs-LDL) particle concentration in the plasma sample by detecting and counting the fractionated lipoprotein particles having a particle diameter of 180.0-208.2 A;
   d. determining a large low density lipoprotein (l-LDL) particle concentration in the plasma sample by detecting and counting the fractionated lipoprotein particles having a particle diameter of 220.0-233.3 A; and
   e. identifying the MHD patient as having:
   i. increased risk of mortality when the sample vs-LDL particle concentration is greater than a reference vs-LDL particle concentration;
   ii. reduced risk of mortality when the sample l-LDL particle concentration is greater than a reference l-LDL particle concentration; or
   iii. no change in the risk of mortality when the sample vs-LDL particle concentration is less than or equal to the reference vs-LDL particle concentration and the sample l-LDL particle concentration is less than the reference l-LDL concentration,
   whereby a vs-LDL particle concentration in a plasma sample from a MHD patient that is greater than the reference vs-LDL particle concentration and a l-LDL particle concentration in a plasma sample from a MHD patient that is greater than the reference l-LDL particle concentration indicates an reduced risk of mortality in the MHD patient.

2. The method of claim 1, wherein the reference vs-LDL particle concentration level is about 121 nmol/L.

3. The method of claim 1, wherein the reference vs-LDL particle concentration is derived from a control population of subjects not undergoing maintenance hemodialysis.

4. The method of claim 1, wherein the reference vs-LDL particle concentration is the vs-LDL particle concentration measured in the patient at an earlier time.

5. The method of claim 1, wherein the reference vs-LDL particle concentration is the vs-LDL particle concentration measured in the patient prior to receiving treatment.

6. The method of claim 1, wherein reference l-LDL particle concentration is about 105 nmol/L.

7. The method of claim 1, wherein the reference l-LDL particle concentration is derived from a control population of subjects not undergoing maintenance hemodialysis.

8. The method of claim 1, wherein the reference l-LDL particle concentration is the l-LDL concentration measured in a plasma sample from the patient at an earlier time.

9. The method of claim 1, wherein the reference l-LDL particle concentration is the l-LDL concentration measured in a plasma sample from the patient prior to receiving treatment.

10. A method for predicting mortality risk in a maintenance hemodialysis (MHD) patient comprising,
   a. separating lipoprotein particles from non-lipoprotein particles in a plasma sample from an MHD patient;
   b. irradiating with alpha radiation and fractionating the lipoprotein particles according to particle diameter using on mobility lipoprotein fractionation;
   c. determining a small low density lipoprotein (s-LDL) particle concentration in the plasma sample by detecting and counting the fractionated lipoprotein particles having a particle diameter of 208.2-214.1 A;
   d. determining a large low density lipoprotein (l-LDL) particle concentration in the plasma sample by detecting and counting the fractionated lipoprotein particles having a particle diameter of 220.0-233.3 A;
   e. determining a ratio of the sample l-LDL particle concentration to the sample s-LDL particle concentration, and
   f. identifying the MHD patient as having reduced risk of mortality when the sample l-LDL:s-LDL ratio is greater than a reference l-LDL:s-LDL ratio or identifying the MHD patient as having no change in the risk of mortality when the reference LDL:s-LDL ratio is less than the reference ratio.

11. The method of claim 10, wherein the reference l-LDL:s-LDL ratio is about 0.90-1.05.

12. The method of claim 10, wherein the reference l-LDL:s-LDL ratio is derived from a control population of subjects not undergoing maintenance hemodialysis.

13. The method of claim 10, wherein the reference l-LDL:s-LDL ratio is the l-LDL:s-LDL ratio measured in a plasma sample from the patient at an earlier time.

14. The method of claim 10, wherein the reference l-LDL:s-LDL ratio is the l-LDL:s-LDL ratio measured in a plasma sample from the patient prior to receiving treatment.

15. The method of claim 10, further comprising measuring the total concentration of low density lipoprotein (LDL-C) and/or the total particle concentration of low density lipoprotein (LDL-Pc) in the plasma sample.

16. The method of claim 10, further comprising measuring the total concentration of high density lipoprotein (HDL-C), the total particle concentration of high density lipoprotein (HDL-Pc), the concentration of very low density lipoprotein (VLDL) and/or intermediate density lipoprotein (IDL) in the plasma sample.

17. The method of claim 1, further comprising measuring the total concentration of low density lipoprotein (LDL-C) and/or the total particle concentration of low density lipoprotein (LDL-Pc) in the plasma sample.

18. The method of claim 1, further comprising measuring the total concentration of high density lipoprotein (HDL-C), the total particle concentration of high density lipoprotein (HDL-Pc), the concentration of very low density lipoprotein (VLDL) and/or intermediate density lipoprotein (IDL) in the plasma sample.

* * * * *